United States Patent [19]

Davis, deceased et al.

[11] Plant 4,861

[45] Jun. 29, 1982

[54] PEACH TREE (7-7-52)

[75] Inventors: Luther D. Davis, deceased, late of Davis, Calif.; by Donald R. Brooks, executor, West Sacramento, Calif.

[73] Assignee: The Regents of the University of California, Berkeley, Calif.

[21] Appl. No.: 198,915

[22] Filed: Oct. 20, 1980

[51] Int. Cl.[3] ..... A01H 5/03

[52] U.S. Cl. ..... Plt./43

[58] Field of Search ..... Plt./43

*Primary Examiner*—Robert E. Bagwill

*Attorney, Agent, or Firm*—Roger B. Webster

[57] ABSTRACT

A peach tree which is medium size, vigorous, hardy, upright-spreading, foliated with medium size, ovate-lanceolate to lanceolate leaves having a finely crenate margin, medium length petiole, and reniform glands; blooms from hardy, medium size, pointed flower buds free from the stem and moderately pubescent, the flowers being medium size, non-showy, and deep rose pink shading lighter at base; and is a regular and highly productive bearer of large, uniform, globose, clingstone fruit having orange buff skin with a red blush, and firm, highly flavored, orange buff flesh.

2 Drawing Figures

CLASSIFICATION OF THE VARIETY

The present variety of peach tree is embraced by Class 43, Plants, of the U.S. Patent Office Manual of Classification.

BACKGROUND OF THE VARIETY

1. Field of the Invention

The inventor, Luther D. Davis, in the conduct of an extensive plant breeding program, originated a substantial number of new and distinct varieties of fruit trees, and which included the herein-claimed variety of peach tree. Such plant breeding program was undertaken by inventor Luther D. Davis at the University of California, Davis, Yolo County, Calif., and particularly in the experimental orchard at such location.

2. Prior Varieties

Among existing varieties of peach trees known to inventor Luther D. Davis, particular reference is made to Carolyn (an unpatented selection of the U.S. Department of Agriculture), and Loadel (unpatented) hereinafter mentioned for the purpose of comparison.

ORIGIN OF THE VARIETY

The present variety of peach tree was originated by inventor Luther D. Davis in the aforesaid experimental orchard, as a cross between two unnamed peach seedlings, which bore the identifications D25-9E and G40-5E.

ASEXUAL REPRODUCTION OF THE VARIETY

Subsequent to its origination, the present variety of peach tree was asexually reproduced, on behalf of inventor Luther D. Davis, and by budding on peach seedling rootstock, by a commercial nursery. Such asexual reproductions, in maturity at certain test plots, ran true to the original tree of the variety in all respects.

SUMMARY OF THE VARIETY

The present variety of peach tree is medium size, vigorous, hardy, upright-spreading, foliated with medium size, ovate-lanceolate to lanceolate leaves having a finely crenate margin, medium length petiole, and reniform glands; blooms from hardy, medium size, pointed flower buds free from the stem and moderately pubescent, the flowers being medium size, non-showy, and deep rose pink shading lighter at base; and is a regular and highly productive bearer of large, uniform, globose, clingstone fruit having orange buff skin with a red blush, and firm, highly flavored, orange buff flesh.

The present variety of peach tree bears clingstone fruit which ripens approximately with the Carolyn and is similar in shape, but is distinctive, in comparison, by not dropping fruit before harvest, by less blush on the skin, by a stone which is eroded near the apex of the dorsal side, and by leaf glands which are reniform and not globose as are those of the Carolyn.

The present variety of peach tree is further characterized by fruit of a size and firmness superior for processing by canning, and the fruit as canned having an excellent flavor and attractive appearance.

BRIEF DESCRIPTION OF THE DRAWING

The drawing is an illustration, by photographic reproduction in color, of separate fruit of the variety; one fruit being half cut away and the stone removed to show the flesh and the pit cavity. The drawing also illustrates separate stones of the variety.

DESCRIPTION OF THE VARIETY

The botanical details of this new and distinct variety of peach tree—with color definitions (except those in common color terms) referenced to Ridgway, Color Standards and Color Nomenclature (1912 edition)—are as follows:

Tree:
- *Size.*—Medium.
- *Vigor.*—Vigorous.
- *Growth.*—Upright — spreading.
- *Hardiness.*—Hardy.
- *Production.*—Very productive.
- *Bearing.*—Regular bearer.

Trunk:
- *Size.*—Medium.
- *Texture.*—Medium.

Branches:
- *Size.*—Medium.
- *Surface texture.*—Medium.

*Color.*—New branches: light brown (Dresden Brown — Plate XV). Older branches: darker brown (Raw Umber — Plate III); finish — dull. Current season's shoots: light green (Courge Green — Plate XVII); well tinged with red on exposed surfaces.

*Lenticels.*—Number: Medium. Size: medium.

Leaves:

*Size.*—Medium. Average length from vigorous shoots — 16.4 cm. Average length from average shoots — 14.7 cm. Average width from vigorous shoots — 4.6 cm. Average width from average shoots — 3.9 cm. Length/width ratio is 3.6 for vigorous shoots and 3.8 for average shoots.

*Form.*—Ovate lanceolate to lanceolate.

*Apex.*—Acuminate to attenuate.

*Thickness.*—Blade thin, flat to moderately folded and often moderately twisted on midshoot leaves.

*Color.*—Top side — green (Cerro Green — Plate V). Under side — green (Grape Green — Plate XLI).

*Margin.*—Finely crenate. Straight or moderately wavy.

*Petiole.*—Medium length — average 1.2 cm. on vigorous growth.

*Glands.*—Reniform. Average number — 4–6. Position — 2–4 commonly on petiole and 2 on base of blade.

Flower buds:

*Hardiness.*—Hardy.

*Size.*—Medium.

*Length.*—Medium.

*Form.*—Pointed. Free from stem.

*Pubescence.*—Medium.

Flowers:

*Blooming period.*—Medium late season — about with Loadel.

*Size.*—Medium. Diameter of fully open flowers — 26–29 mm. Petal length — 12–13 mm. Petal width — 8–9 mm. Petals tend to roll laterally inward from sides.

*Color of petals.*—Pink (Deep Rose Pink — Plate XII), shading lighter at base.

*Stamens.*—Number — 25–30. Length — 10–15 mm.

*Anthers.*—Red dorsally.

*Calyx lobes.*—Length — 5 mm. Width — 4 mm.

*Nectaries.*—Orange.

*Type.*—Non-showy.

*Number.*—Usually 2 per node.

Fruit:

*Maturity when described.*—Canning ripe — Aug. 3, 1979; 75% standard California cling peach maturity disc, 25% Dixon disc. Average firmness — 10.5 pounds pressure test. Average firmness — 9.0–10.5 pounds pressure when 90–99% of the fruit show flesh color equal to or darker than standard California cling peach maturity disc.

*Season of maturity.*—With or one day ahead of Carolyn.

*Size.*—Uniform. Large for a late-season clingstone peach. Average diameter axially — 73.9 mm. Average transversely in suture plane — 76.5 mm. Average cheek to cheek — 79.8 mm.

*Form.*—Uniform. Slightly asymmetrical. Globose.

*Suture.*—Distinct. Shallow. Extends to apex with slight depression beyond pistil point.

*Ventral surface.*—Slightly rounded. Often lipped on one side only. Lip most pronounced at mid-point on suture line.

*Base.*—Rounded to weakly oblique.

*Cavity.*—Cuneate. Narrowly elliptical. Depth — 16–17 mm. Width — 15–18 mm. Length — 30–35 mm. Heavily creased toward ventral suture. Lightly creased toward dorsal side.

*Apex.*—Rounded.

*Pistil point.*—Occasionally oblique.

Skin:

*Thickness.*—Thick.

*Texture.*—Tough.

*Tenacity.*—Tenacious to flesh.

*Tendency to crack.*—None.

*Pubescence.*—Medium. Short.

*Color.*—Ground Color — golden yellow (Orange buff — Plate III). Blush Color — Red (Acajou Red — Plate XIII).

Flesh:

*Color.*—Golden yellow (Orange buff — Plate III).

*Amygdalin.*—Scant.

*Juice.*—Moderate.

*Texture.*—Fine. Non-melting. Firm.

*Fibers.*—None.

*Ripens.*—Evenly.

*Flavor.*—Mild.

*Canning quality.*—Excellent.

*Aroma.*—Mild.

*Eating quality.*—Excellent.

Stone:

*Type.*—Cling.

*Size.*—Medium. Average length — 37 mm. Average breadth — 27 mm. Average thickness — 20 mm.

*Form.*—Irregular. Roughly obovate.

*Base.*—Slightly oblique, shorter on ventral shoulder.

*Hilum.*—Medium size. Narrow. Oblong.

*Apex.*—Generally rounded, but heavily eroded on upper dorsal edge.

*Tip.*—Acuminate.

*Sides.*—Equal.

*Surface.*—Moderately pitted and grooved. Regularly grooved near base and along ventral edge.

*Pits.*—Pitted in central area of stone and extending into dorsal shoulder area. Shape: Variable, but predominately rounded or oval.

*Ridges.*—Low. Rounded.

*Ventral suture.*—Narrow, with somewhat low flattened wings converging apically. Basal one-third moderately eroded.

*Dorsal edge.*—Very irregular, with an area of the suture just below the apex tip heavily eroded so as to present a concave-shaped depression along one-quarter of the upper dorsal suture. From the lower margin of the concave area, the dorsal edge is full and moderately winged, with a deep groove extending to the base.

*Color.*—Brown (Cinnamon — Plate XXIX).

*Tendency to split.*—Slight.

Use:

*Major use.*—Canning.

Keeping quality: Good.

Resistance to insects and diseases: Average.

The peach tree and its fruit herein described may vary in slight detail due to climatic and soil conditions under which the variety may be grown; the present description being of the variety as grown in the Central Valley of California.

It is claimed:

1. A new and distinct variety of peach tree, substantially as illustrated and described, which regularly and with high productivity bears large, uniform, globose, clingstone fruit having firm, highly flavored flesh; the fruit, which ripens approximately with the Carolyn and is similar in shape, is particularly distinctive, in comparison, by not dropping fruit before harvest, by less blush on the skin, by a stone which is eroded near the apex of the dorsal side, and by leaf glands which are reniform and not globose as are those of the Carolyn.

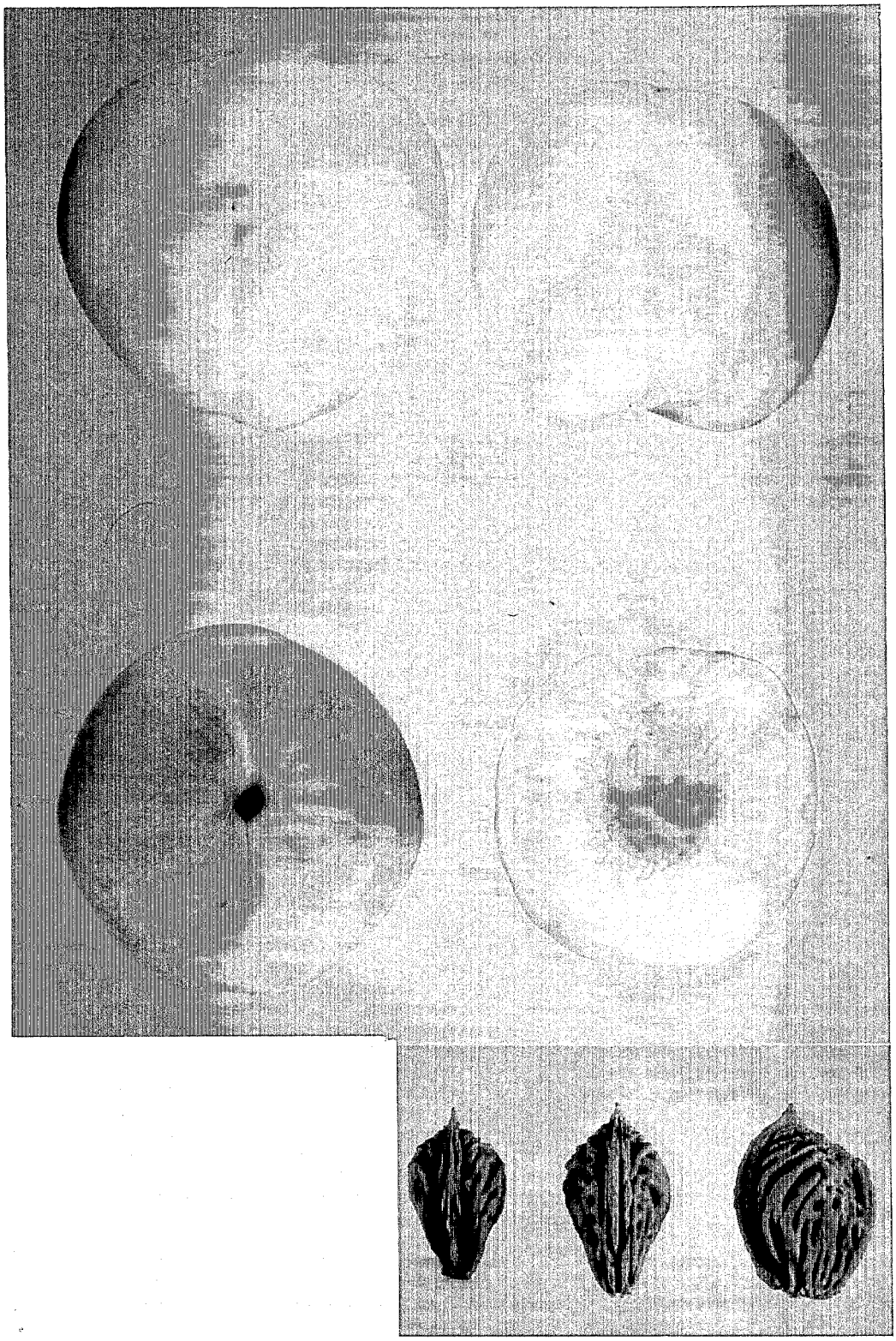

* * * * *